US011696700B2

(12) United States Patent
Rotman et al.

(10) Patent No.: US 11,696,700 B2
(45) Date of Patent: Jul. 11, 2023

(54) SYSTEM AND METHOD FOR CORRECTING FOR PATIENT MOTION DURING MR SCANNING

(71) Applicant: General Electric Company, Schenectady, NY (US)

(72) Inventors: Michael Rotman, Petach-Tikva (IL); Rafael Shmuel Brada, Hod-Hasharon (IL); Sangtae Ahn, Guilderland, NY (US); Christopher Judson Hardy, Schenectady, NY (US); Itzik Malkiel, Givatayim (IL); Ron Wein, Ramat Hasharon (IL)

(73) Assignee: General Electric Company, Schenectady, NY (US)

(*) Notice: Subject to any disclaimer, the term of this patent is extended or adjusted under 35 U.S.C. 154(b) by 931 days.

(21) Appl. No.: 16/394,774

(22) Filed: Apr. 25, 2019

(65) Prior Publication Data
US 2020/0337591 A1 Oct. 29, 2020

(51) Int. Cl.
*A61B 5/055* (2006.01)
*G01R 33/565* (2006.01)
*G01R 33/48* (2006.01)
*G01R 33/56* (2006.01)
*G01R 33/567* (2006.01)

(52) U.S. Cl.
CPC .......... *A61B 5/055* (2013.01); *G01R 33/4818* (2013.01); *G01R 33/56509* (2013.01); *G01R 33/5608* (2013.01); *G01R 33/5676* (2013.01)

(58) Field of Classification Search
CPC ............... A61B 5/055; G01R 33/4818; G01R 33/56509; G01R 33/5608; G01R 33/5676; G06N 3/02; G06N 7/00; G06N 7/046; G06N 20/00
See application file for complete search history.

(56) References Cited

U.S. PATENT DOCUMENTS

| 6,341,179 | B1 | 1/2002 | Stoyle et al. |
| 8,306,299 | B2 | 11/2012 | Samsonov et al. |
| 10,058,287 | B2 | 8/2018 | Meyer et al. |
| 10,453,200 | B2 * | 10/2019 | Mukherjee ............... G06T 7/136 |
| 2009/0316971 | A1 * | 12/2009 | Song ....................... G06T 7/246 382/131 |

(Continued)

FOREIGN PATENT DOCUMENTS

WO 2017223560 A1 12/2017

OTHER PUBLICATIONS

Pipe, James G., "Motion correction with Propeller MRI: Application to head motion and free-breathing cardiac imaging," Magnetic Resonance in Medicine, vol. 42 Issue: 5, pp. 963-969, Nov. 1999.

(Continued)

*Primary Examiner* — Keith M Raymond
*Assistant Examiner* — Sean A Frith

(57) ABSTRACT

K-space data obtained from a magnetic resonance imaging scan where motion was detected is split into two parts in accordance with the timing of the motion to produce first and second sets of k-space data corresponding to different poses. Sub-images are reconstructed from the k first and second sets of k-space data, which are used as inputs to a deep neural network which transforms them into a motion-corrected image.

21 Claims, 12 Drawing Sheets

(56) References Cited

U.S. PATENT DOCUMENTS

| | | | | |
|---|---|---|---|---|
| 2012/0121124 | A1* | 5/2012 | Bammer | G06T 7/248 382/103 |
| 2016/0128606 | A1* | 5/2016 | Sakuragi | A61B 5/055 600/415 |
| 2016/0252596 | A1* | 9/2016 | Nielsen | G01R 33/56509 324/309 |
| 2017/0061620 | A1 | 3/2017 | Park et al. | |
| 2017/0184694 | A1 | 6/2017 | Li et al. | |
| 2017/0358095 | A1* | 12/2017 | Levy | G01R 33/4808 |
| 2018/0144214 | A1* | 5/2018 | Hsieh | G06T 7/0002 |
| 2018/0204358 | A1* | 7/2018 | An | G01R 33/0029 |
| 2018/0293762 | A1 | 10/2018 | Fu et al. | |
| 2018/0360313 | A1* | 12/2018 | Zhang | G06T 7/30 |
| 2019/0244100 | A1* | 8/2019 | Seo | G06N 3/0454 |
| 2019/0257905 | A1* | 8/2019 | Cheng | G01R 33/5608 |
| 2019/0355093 | A1* | 11/2019 | Ye | G06N 3/084 |

OTHER PUBLICATIONS

Andre, et al., "Toward Quantifying the Prevalence, Severity, and Cost Associated With Patient Motion During Clinical MR Examinations," Journal. Am. Coll. Radiol., 12:689-695, vol. 12, No. 7, 7 pages, Jul. 2015.

Oksuz et al., "Cardiac MR Motion Artefact Correction from K-space Using Deep Learning-Based Reconstruction," International Workshop on Machine Learning for Medical Image Reconstruction, vol. 11074, pp. 21-29, Sep. 12, 2018.

Braun, et al., "Wasserstein GAN for Motion Artifact Reduction of MR Images," Medical Imaging Technologies, Siemens Healthineers, Princeton, NJ, United States, https://index.mirasmart.com/ISMRM2018/PDFfiles/4093.html, 3 pages.

Johnson, et al., "Motion correction in MRI using deep learning," Proc. Intl. Soc. Mag. Reson. Med. 26 (2018), https://index.mirasmart.com/ISMRM2018/PDFfiles/4098.html, 2 pages.

Pawar, et al., "Motion Correction in MRI using Deep Convolutional Neural Network," Proc. Intl. Soc. Mag. Reson. Med. 26 (2018), https://index.mirasmart.com/ISMRM2018/PDFfiles/1174.html, 3 pages.

Sommer, et al., "Correction of motion artifacts using a multi-resolution fully convolutional neural network," Proc. Intl. Soc. Mag. Reson. Med. 26 (2018), https://index.mirasmart.com/ISMRM2018/PDFfiles/1175.html, 2 pages.

* cited by examiner

SYSTEM AND METHOD FOR CORRECTING FOR PATIENT MOTION DURING MR SCANNING

BACKGROUND

In general, magnetic resonance imaging (MRI) examinations are based on the interactions among a primary magnetic field, a radiofrequency (RF) magnetic field and time varying magnetic gradient fields with gyromagnetic material having nuclear spins within a subject of interest, such as a patient. Certain gyromagnetic materials, such as hydrogen nuclei in water molecules, have characteristic behaviors in response to external magnetic fields. The precession of spins of these nuclei can be influenced by manipulation of the fields to produce RF signals that can be detected, processed, and used to reconstruct a useful image.

Patient motion is one of the biggest sources of inefficiency in clinical MRI, often requiring re-scans or even second visits by the patient. In particular, patient motion can cause blurriness, artifacts, and other inconsistencies in MR images. Certain approaches to correct motion require either some sort of hardware for monitoring the motion (adding to cost and patient setup time), navigator sequences (which take time away from the imaging sequence), or particular types of acquisitions which can limit the type of information that can be collected. Accordingly, a need exists for improved methods for data acquisition and reconstruction in magnetic resonance imaging that are robust to patient motion.

BRIEF DESCRIPTION

In one embodiment, a magnetic resonance imaging (MRI) method includes dividing k-space data from a motion-corrupted MRI scan into a first portion and a second portion based on timing associated with a transition between poses and a predetermined scan order, wherein the predetermined scan order defines how k-space is filled as a function of time step for the motion-corrupted MRI scan; reconstructing a first sub-image and a second sub-image from the first portion and the second portion, respectively; providing the first sub-image and the second sub-image as inputs to a neural network; and transforming the first sub-image and the second sub-image into a motion-corrected image using the neural network.

In another embodiment, a magnetic resonance imaging (MRI) method includes producing a first sub-image and a second sub-image from a motion-corrupted set of k-space data representing a plurality of poses for an imaged subject via a process. The process includes identifying a portion of the motion-corrupted set of k-space data corresponding to a dominant pose; generating the first sub-image from the identified portion of the motion-corrupted set of k-space data; grouping remaining portions of the motion-corrupted set of k-space data corresponding to other poses together; and generating the second sub-image from the remaining portions of the motion-corrupted set of k-space data. The method includes inputting the first sub-image and the second sub-image to a neural network trained to transform pairs of motion-corrupted sub-images into motion-corrected images; and transforming the first sub-image and the second sub-image into a motion-corrected image using the neural network.

In a further embodiment, a magnetic resonance imaging (MRI) reconstruction module includes circuitry programmed to implement a trained neural network for transformation of motion-corrupted images into motion-corrected images. The module also includes a plurality of iteration blocks of the trained neural network to receive a first sub-image corresponding to a first pose and a second sub-image corresponding to at least a second pose as inputs, and to output a motion-corrected image. The module further includes a data consistency block of each iteration block of the plurality of iteration blocks, wherein the data consistency block is programmed to produce a reconstructed image where line locations in k-space that correspond to the first pose are overwritten with k-space data from the first pose.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

As set forth above, patient motion is one of the biggest sources of inefficiency in clinical MRI, often requiring re-scans or even second visits by the patient. Research has shown that patient motion can lead to repeated acquisition sequences in as much as 20% of MRI exams. This results in significant annual losses for every scanner as throughput is reduced.

Disclosed embodiments include a system and method for correcting for patient motion occurring during an MRI scan. The system and method use the timing of the patient motion during the scan to break k-space data into two or more parts. This may include the part collected before the patient movement and the part after, or some other division of the k-space data depending on when one or more motion events occurred and the signal energy associated with the resulting different motion states, otherwise referred to herein as "poses." In particular, a pose as disclosed herein is intended to denote a position of the subject being imaged that corresponds to the portion of k-space being acquired at a given time (or time step, as described below). Using the two or more parts, a corrected image is calculated using a deep-learning neural network.

Figure 1:
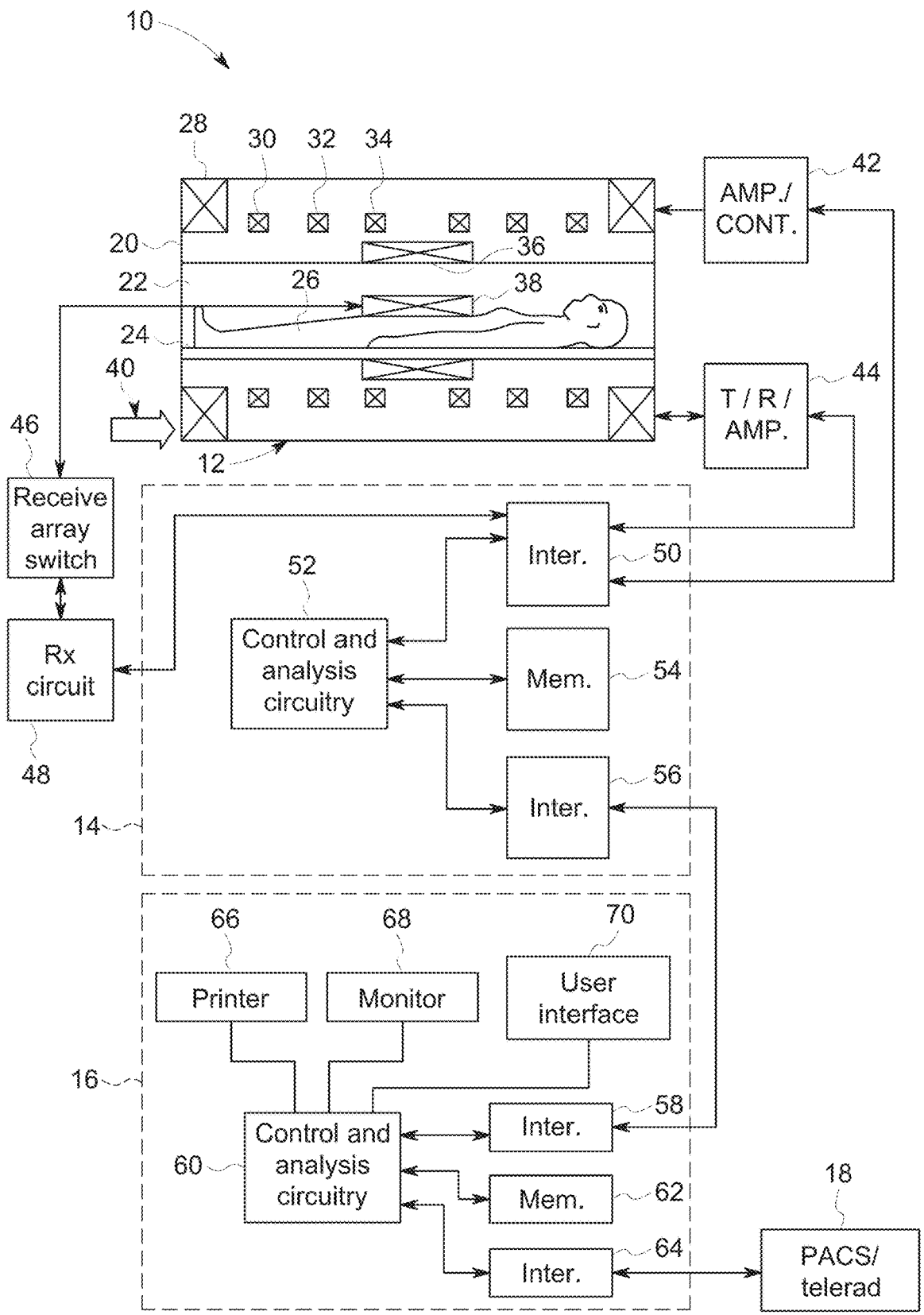
FIG. 1 is a diagrammatic illustration of an embodiment of a magnetic resonance imaging system configured to perform the data acquisition, motion detection, and image reconstruction described herein.

An example system for performing the techniques described herein is discussed with respect to FIG. 1. The embodiments described herein may be performed by a magnetic resonance imaging (MRI) system, wherein specific imaging routines (e.g., accelerated imaging routines for MRI sequences) are initiated by a user (e.g., a radiologist). Further, the MRI system may perform data acquisition, data reconstruction, and image synthesis. Accordingly, referring to FIG. 1, a magnetic resonance imaging system 10 is illustrated schematically as including a scanner 12, a scanner control circuit 14, and a system control circuitry 16. According to the embodiments described herein, the MRI system 10 is generally configured to perform MR imaging, such as imaging sequences with adaptive motion correction, various weighting techniques, fluid attenuation techniques, perfusion techniques, tensor imaging, and so on. System 10 additionally includes remote access and storage systems or devices such as picture archiving and communication systems (PACS) 18, or other devices such as teleradiology equipment so that data acquired by the system 10 may be accessed on- or off-site. In this way, acquired data may be acquired, followed by on- or off-site processing and evaluation. While the MRI system 10 may include any suitable scanner or detector, in the illustrated embodiment, the system 10 includes a full body scanner 12 having a housing 20 through which a bore 22 is formed. A table 24 is moveable into the bore 22 to permit a patient 26 to be positioned therein for imaging selected anatomy within the patient.

Scanner 12 includes a series of associated coils for producing controlled magnetic fields for exciting the gyromagnetic material within the anatomy of the subject being imaged. Specifically, a primary magnet coil 28 is provided for generating a primary magnetic field generally aligned with the bore 22. A series of gradient coils 30, 32, and 34 permit controlled magnetic gradient fields to be generated for positional encoding of certain of the gyromagnetic nuclei within the patient 26 during examination sequences. A radio frequency (RF) coil 36 is provided, and is configured to generate radio frequency pulses for exciting the certain gyromagnetic nuclei within the patient. In addition to the coils that may be local to the scanner 12, the system 10 also includes a set of receiving coils 38 (e.g., a phased array of coils) configured for placement proximal (e.g., against) the patient 26. The receiving coils 38 may have any geometry, including both enclosed and single-sided geometries. As an example, the receiving coils 38 can include cervical/thoracic/lumbar (CTL) coils, head coils, single-sided spine coils, and so forth. Generally, the receiving coils 38 are placed close to or on top of the patient 26 so as to receive the weak RF signals (weak relative to the transmitted pulses generated by RF coil 36) that are generated by certain of the gyromagnetic nuclei within the patient 26 as they return to their relaxed state. The receiving coils 38 may be switched off so as not to receive or resonate with the transmit pulses generated by the scanner coils, and may be switched on so as to receive or resonate with the RF signals generated by the relaxing gyromagnetic nuclei.

The various coils of system 10 are controlled by external circuitry to generate the desired field and pulses, and to read emissions from the gyromagnetic material in a controlled manner. In the illustrated embodiment, a main power supply 40 provides power to the primary field coil 28. A driver circuit 42 is provided for pulsing the gradient field coils 30, 32, and 34. Such a circuit may include amplification and control circuitry for supplying current to the coils as defined by digitized pulse sequences output by the scanner control circuit 14. Another control circuit 44 is provided for regulating operation of the RF coil 36. Circuit 44 includes a switching device for alternating between the active and inactive modes of operation, wherein the RF coil 36 transmits and does not transmit signals, respectively. Circuit 44 also includes amplification circuitry for generating the RF pulses. Similarly, the receiving coils 38 are connected to switch 46 that is capable of switching the receiving coils 38 between receiving and non-receiving modes such that the receiving coils 38 resonate with the RF signals produced by relaxing gyromagnetic nuclei from within the patient 26 while in the receiving state, and they do not resonate with RF energy from the transmitting coils (i.e., coil 36) so as to prevent undesirable operation while in the non-receiving state. Additionally, a receiving circuit 48 is provided for receiving the data detected by the receiving coils 38, and may include one or more multiplexing and/or amplification circuits.

It should be noted that while the scanner 12 and the control/amplification circuitry described above are illustrated as being coupled by a single line, that many such lines may occur in an actual instantiation. For example, separate lines may be used for control, data communication, and so on. Further, suitable hardware may be disposed along each type of line for the proper handling of the data. Indeed, various filters, digitizers, and processors may be disposed between the scanner and either or both of the scanner and system control circuitry 14, 16. By way of non-limiting example, certain of the control and analysis circuitry described in detail below, although illustrated as a single unit, includes additional hardware such as image reconstruction hardware configured to perform the motion correction and image reconstruction techniques described herein. Further, in certain embodiments, the control and analysis circuitry described herein may be associated with a trained neural network used for motion detection and/or another trained neural network used for image reconstruction. Indeed, where a neural network is described in the present disclosure, it should be noted that the neural network may be associated with (e.g., a part of or connected to) the MRI system 10. The neural network may, for example, be implemented as specific hardware components (e.g., specialized processors), or may be implemented as software via an emulation on a computing platform. In one embodiment of the present disclosure, for instance, a magnetic resonance imaging (MRI) reconstruction module may include programming to implement a trained neural network, meaning that the neural network may be part of the module either as logic or stored sets of instructions (e.g., in software).

As illustrated, scanner control circuit 14 includes an interface circuit 50 which outputs signals for driving the gradient field coils and the RF coil and for receiving the data representative of the magnetic resonance signals produced in examination sequences. The interface circuit 50 is coupled to a control and analysis circuit 52. The control and analysis circuit 52 executes the commands for driving the circuit 42 and circuit 44 based on defined protocols selected via system control circuit 16. Control and analysis circuit 52 also serves to receive the magnetic resonance signals and performs subsequent processing before transmitting the data to system control circuit 16. Scanner control circuit 14 also includes one or more memory circuits 54, which store configuration parameters, pulse sequence descriptions, examination results, and so forth, during operation. Interface circuit 56 is coupled to the control and analysis circuit 52 for exchanging data between scanner control circuit 14 and system control circuit 16. Such data will typically include selection of specific examination sequences to be performed, configuration parameters of these sequences, and acquired data, which may be transmitted in raw or processed form from scanner control circuit 14 for subsequent processing, storage, transmission and display. Therefore, in certain embodiments, the control and analysis circuit 52, while illustrated as a single unit, may include one or more hardware devices.

System control circuit 16 includes an interface circuit 58, which receives data from the scanner control circuit 14 and transmits data and commands back to the scanner control circuit 14. The interface circuit 58 is coupled to a control and analysis circuit 60 which may include a CPU in a multipurpose or application specific computer or workstation. Control and analysis circuit 60 is coupled to a memory circuit 62 to store programming code for operation of the MRI system 10 and to store the processed image data for later reconstruction, display and transmission. The programming code may execute one or more algorithms capable of performing, by way of example, non-Cartesian imaging sequences and processing sampled image data (e.g., blades of data, undersampled data, fluid attenuated data), which will be discussed in detail below. An additional interface circuit 64 may be provided for exchanging image data, configuration parameters, and so forth with external system components such as remote access and storage devices 18.

Finally, the system control and analysis circuit 60 may include various peripheral devices for facilitating operator interface and for producing hard copies of the reconstructed images. In the illustrated embodiment, these peripherals include a printer 60, a monitor 62, and user interface 64 including devices such as a keyboard or a mouse.

Scanner 12 and the control and analysis circuit 52 associated therewith produce magnetic fields and radio frequency pulses in a controlled manner to excite and encode specific gyromagnetic material within the patient 26. The scanner 12 and control and analysis circuit 52 also sense the signals emanating from such material and create an image of the material being scanned. In certain embodiments, the scan may include fast-spin-echo (FSE), or gradient-echo (GRE) scan sequences, and the like. It should be noted that the MRI system described is merely intended to be exemplary only, and other system types, such as so-called "open" MRI systems may also be used. Similarly, such systems may be rated by the strength of their primary magnet, and any suitably rated system capable of carrying out the data acquisition and processing described below may be employed.

Specifically, aspects of the present disclosure include methods for acquiring magnetic resonance data and processing of such data to construct one or more motion-corrected images. At least a portion of the disclosed methods may be performed by the system 10 described above with respect to FIG. 1. That is, the MRI system 10 may perform the acquisition techniques described herein, and, in some embodiments, the data processing techniques described herein. It should be noted that subsequent to the acquisitions described herein, the system 10 may simply store the acquired data for later access locally and/or remotely, for example in a memory circuit (e.g., memory 62). Thus, when accessed locally and/or remotely, the acquired data may be manipulated by one or more processors contained within an application-specific or general purpose computer. The one or more processors may access the acquired data and execute routines stored on one or more non-transitory, machine readable media collectively storing instructions for performing methods including the motion detection, image processing, and reconstruction methods described herein.

Indeed, as noted above, disclosed embodiments include circuitry with specific programming to carry out k-space and image-space data processing, image reconstruction, and neural network implementation. Such circuitry may be a part of the control and analysis circuitry of the MRI system 10, such as a module that is implemented as software (e.g., a set of instructions that are executable by a processor and stored on a memory device), or as specific hardware (e.g., a graphics processing unit (GPU), an application-specific processor). In one embodiment, the module may be an MRI reconstruction module.

To facilitate presentation of certain of the embodiments described herein, example acquisition and reconstruction sequences are described below. However, disclosed embodiments are not limited to such acquisitions and sequences, unless explicitly stated otherwise. In certain embodiments, 2D MR images are generated from Cartesian k-space, using either gradient-echo (GRE) or fast-spin-echo (FSE) pulse sequences, and acquired with the RF receiver coil array 38, which may include a plurality of (e.g., 8 or more) coils. Each of the coils has a corresponding spatially varying sensitivity to RF signals generated during acquisition, and the sensitivity of each coil may be mapped to generate sensitivity maps for the coil array. Image reconstruction may involve the generation of a partial image corresponding to each coil by 2D Fourier transformation of the data obtained by a particular coil (referred to as "coil data"), and multiplication by the conjugate of the coil's sensitivity map. To generate a full image, these partial images are summed and the result divided by the sum of squares of the coil sensitivity maps to give the final image. When a patient moves during the scan, the coil data contain a mixture of Fourier components from two or more poses (i.e., motion states). For example, a first pose may be a pre-motion state, and a second pose may be a post-motion state. An image produced from these multiple poses would be corrupted and contain motion-related artifacts. Such an image may be referred to as a "motion-corrupted" image.

Disclosed embodiments include, as noted, systems and methods to produce a motion-corrected image using known timing associated with motion, as well as a neural network trained to transform motion-corrupted images produced from the scan (referred to herein as a "motion-corrupted scan") in which motion occurred into a motion-corrected image. As discussed in further detail below, in one embodiment, the neural network is trained to transform groups (e.g., pairs) of motion-corrupted images into a single motion-corrected image. The pairs of motion-corrupted images are, in certain embodiments, produced by dividing k-space data into separate portions that are associated with different poses, and reconstructing the images from the portions of k-space data.

To help illustrate how this is performed, reference is made to an example MRI sequence involving an example k-space trajectory. For example, certain MRI techniques involve the use of the gradient field coils 30, 32, and/or 34 to traverse Cartesian k-space, and may involve data acquisition via multiple spin excitations or shots, where each shot corresponds to multiple lines of k-space. The shots are spread in time and are thus susceptible to artifacts caused by any motion that may occur between the shots. Disclosed embodiments may include utilizing the timing information of motion that may have occurred during a scan according to a scan order defining phase-encode number as a function of time step. For instance, the MRI reconstruction module of the present disclosure may divide k-space data into different portions according to the scan order and the timing of the motion.

Figure 2:
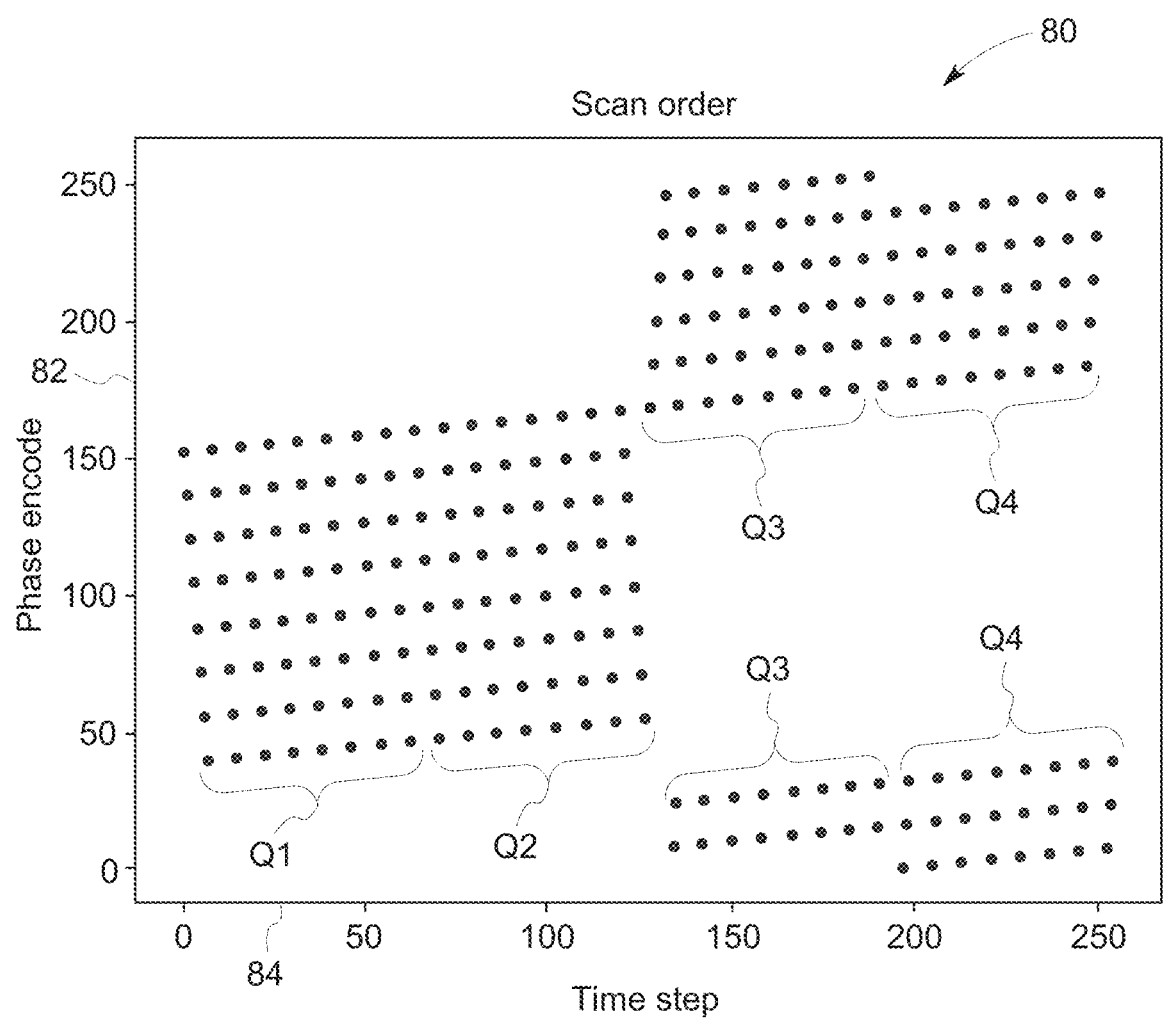
FIG. 2 is a plot depicting an embodiment of a scan order having phase encode as a function of time step.
Figure 3A:
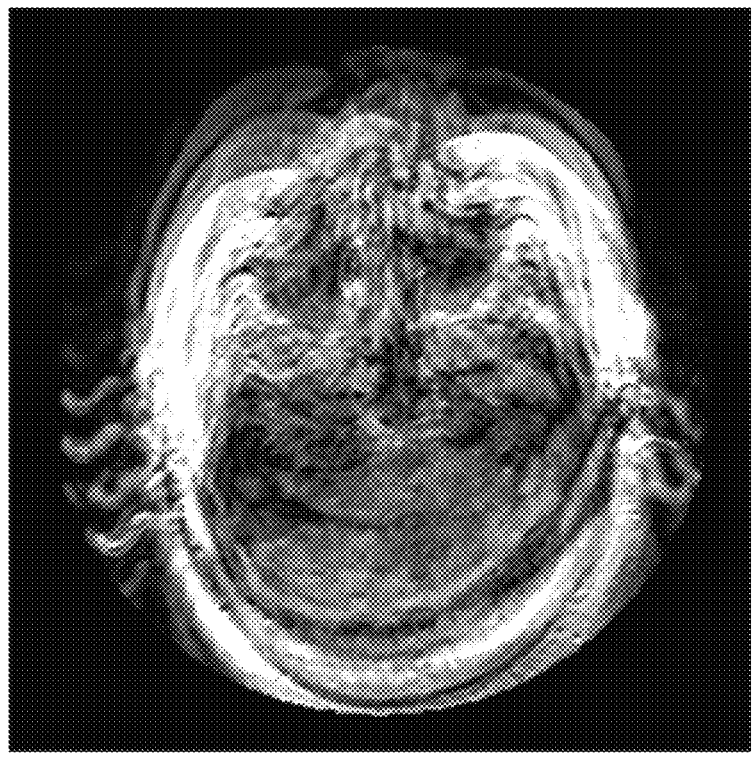
FIGS. 3A-3E provide an example of the effect of motion on images produced from k-space datasets where motion occurred at a different time step of the scan order used to obtain the k-space datasets.
Figure 3B:
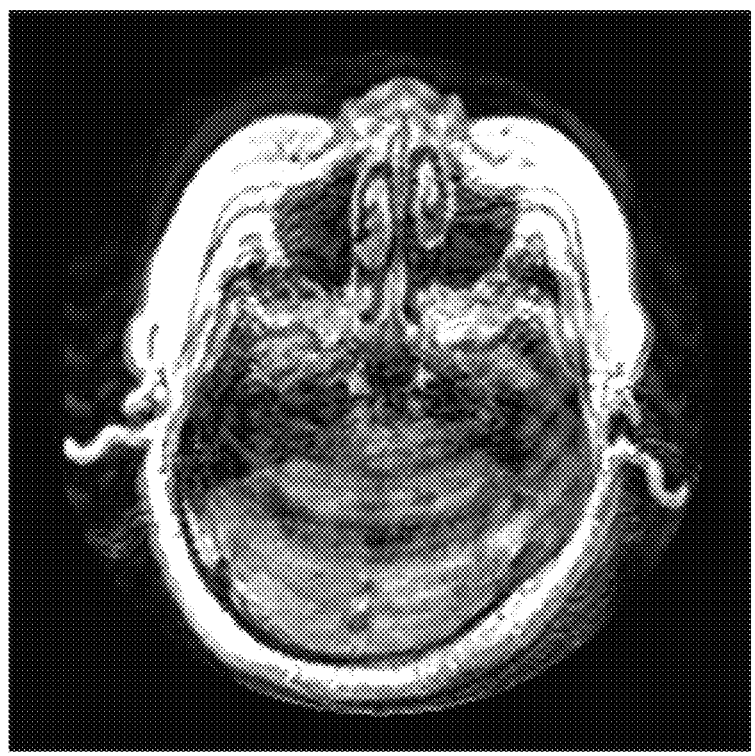
Figure 3C:
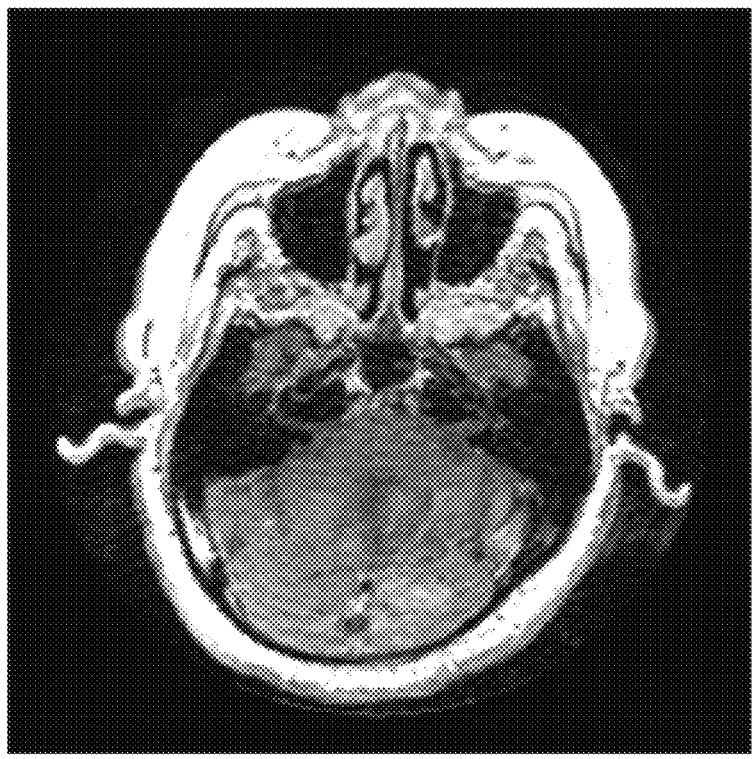
Figure 3D:
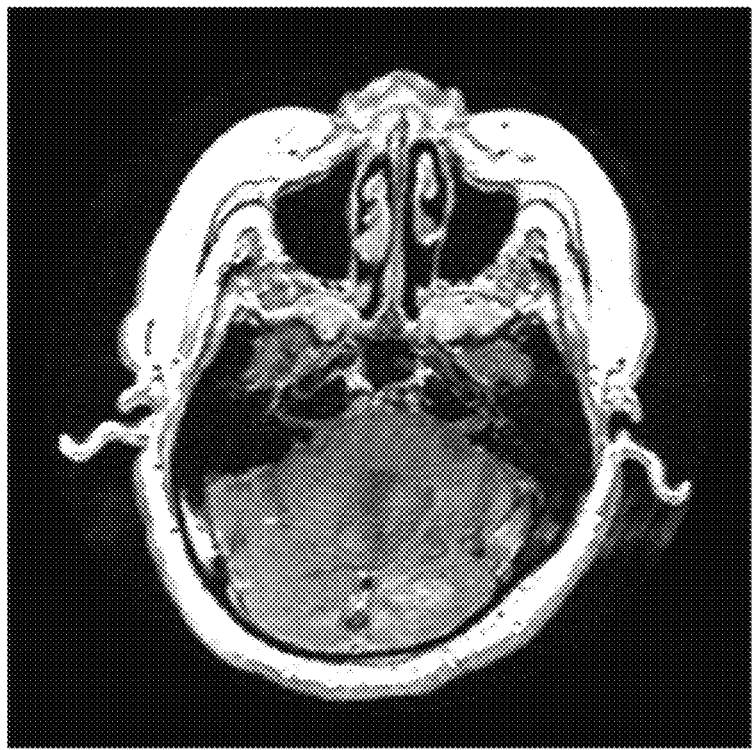
Figure 3E:
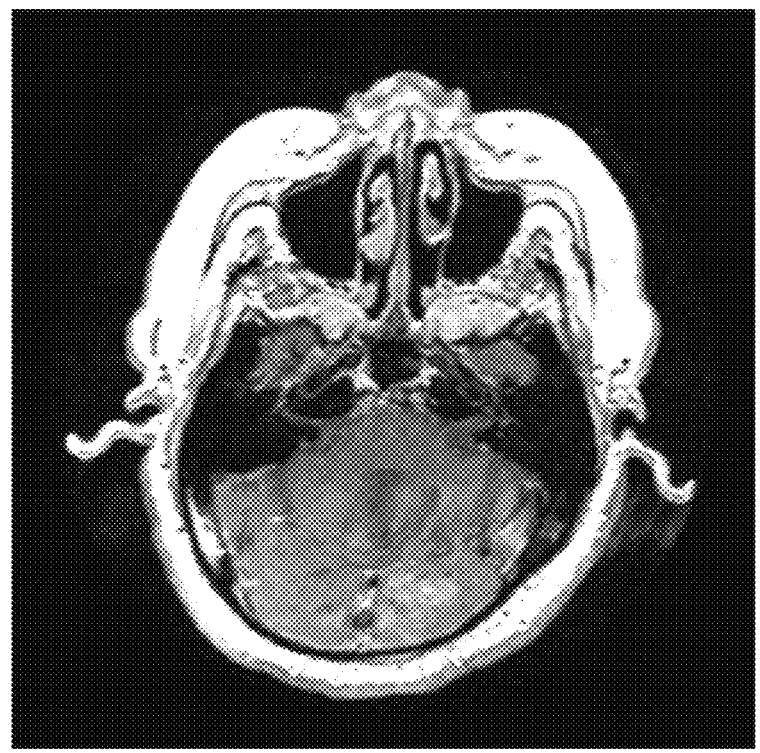

An example of a scan order 80 (or k-space ordering, in this case a T1-FLAIR acquisition) is illustrated in FIG. 2, which depicts phase-encode number 82 as a function of time step 84 (i.e., how phase encodes are filled in k-space as a function of time step). In the illustrated embodiment, 8 lines of k-space are filled for every shot. That is, the echo train length (ETL) in this example is 8. What this means in terms of the order in which k-space is filled is that there is a period of 8 before coming back to scan the adjacent phase encode. There is also typically a delay between each shot, during which the spins can relax towards equilibrium and signals from other imaging slices can be acquired.

As set forth above, disclosed embodiments involve separating portions of k-space data based on the timing associated with motion in accordance with a scan order. An example of the manner in which the k-space data may be divided is depicted in the scan order 80 of FIG. 2. Here, the k-space data are divided into four equal quarters ("quartiles"): Q1 (timestep 1-64), Q2 (timestep 65-128), Q3 (timestep 129-192), and Q4 (timestep 193-256). As shown, for Q1 and Q2, the bulk of the signals are acquired toward the center of k-space, while for Q3 and Q4, the signals are acquired toward the k-space edges.

Motion between shots results in inconsistent poses in different parts of k-space, and thus, blurring and ghosting, as seen in FIGS. 3A-3E. Because the signal energy is greater in central parts of k-space, the motion artifacts tend to be stronger if the patient motion occurred when central k-space was being scanned. Because of this, motion occurring in the timesteps corresponding to Q1 or Q2 would be expected to have a bigger effect on image quality compared to if the motion had occurred in Q3 or Q4. Indeed, FIGS. 3A-3E depict a comparison of images produced by simulating motion during Q1 (a), during Q2 (b), during Q3 (c), during Q4 (d), and the original, unperturbed image (e). Images (a) and (b) have readily apparent image artifacts, and the nature of the motion-related artifacts between the images (a)-(d) varies due to the portion of k-space being filled at the time the motion occurred.

The motion timing may be obtained in a number of ways. For example, navigator sequences may be performed to obtain the timing information. Additionally, or alternatively, various tracking hardware may be used in combination with the MRI system 10, such as a respiration belt, or optical tracking hardware that provides motion information to the control and analysis circuitry of the MRI system 10. Further still, motion information may be obtained by other methods, such as using a deep-learning neural network to identify the presence and timing of motion.

Figure 4:
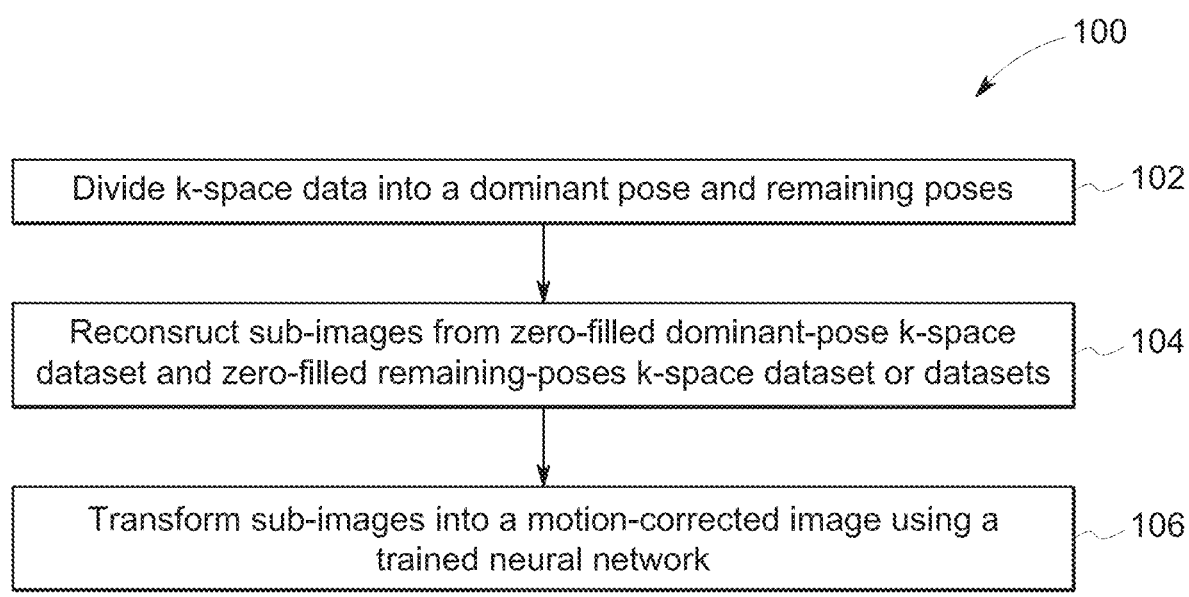
FIG. 4 is a process flow diagram of an embodiment of a method for reconstructing a motion artifact-free image by first dividing k-space data into a first portion corresponding to a single pose, and a second portion corresponding to remaining poses.

Regardless of the manner in which motion timing is obtained, the disclosed embodiments use this timing to produce a motion-corrected image in accordance with the process illustrated in FIG. 4. In particular, FIG. 4 is a process flow diagram of a method 100 for reconstructing a motion artifact-free image by first dividing k-space data (block 102) into a first portion corresponding to a single pose, and a second portion corresponding to remaining poses (e.g., one or more different poses that have been aggregated). The method 100 may be performed by the control and analysis circuitry of the MRI system 10, such as the MRI reconstruction module described above.

In certain embodiments, the acts represented by block 102 may include dividing the k-space data into a first portion corresponding to a dominant pose and a second portion corresponding to all remaining poses. Because the motion may occur at any point during the scan, i.e., during or between any one of Q1-Q4, the division of the k-space data may not simply be between the quartiles. Instead, the division may occur within one of the quartiles such that the first portion includes k-space data from only a portion of one of the quartiles, either alone or in combination with multiple of the quartiles. In certain embodiments, for example, there may be multiple poses resulting from patient motion occurring between different time steps. In such embodiments, the dominant pose may be chosen as the pose with the dominant signal in the center of k-space, with all other segregated k-space regions corresponding to other poses, in some embodiments, being grouped together as an aggregated k-space. As discussed below, it may be desirable to choose the first portion in this manner to allow the dominant pose to be used as a constraint in the reconstruction and motion correction process.

Once the k-space data have been divided, the method 100 includes reconstructing (block 104) sub-images from the dominant pose k-space data and the aggregate of the remaining poses' k-space data. For example, the acts of block 104 may include zero-filling portions of k-space for each of the dominant pose and remaining pose datasets in locations where there is no k-space filling, followed by transformation to the image domain (e.g., via Fast Fourier Transform (FFT))

of the zero-filled datasets, and coil combining as described above to produce the first sub-image and the second sub-image as complex images. The images produced according to this technique are referred to herein as "sub-images" because, although they are actual images, they are constructed using a divided, zero-filled set of less than all the acquired k-space data.

Figure 5A:
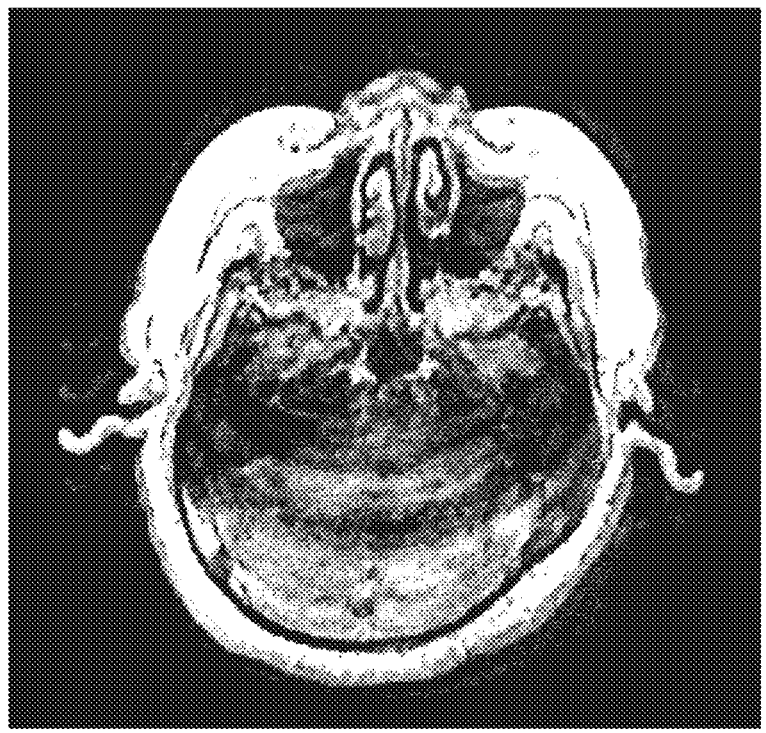
FIGS. 5A and 5B are an example first sub-image and an example second sub-image, respectively, produced using separate portions of k-space data in accordance with the method of FIG. 4.
Figure 5B:
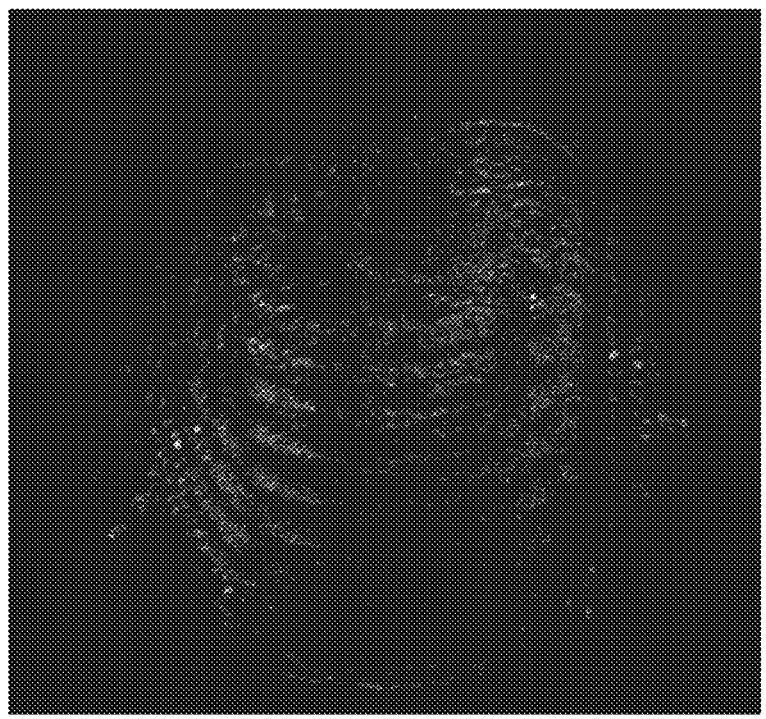

Examples of two such images generated as an output from the acts of block 104 are shown in FIGS. 5A and 5B. In particular, in FIGS. 5A and 5B, image (a) is a pre-motion zero-filled sub-image, which in this example corresponds to the dominant pose, and image (b) is a post-motion zero-filled sub-image, which in this example corresponds to the aggregated remaining poses. In this example, motion occurred in Q2.

Returning to method 100, the two sub-images are transformed (block 106) into a motion-corrected image using a deep-learning neural network. In particular, the first sub-image and the second sub-image are used as inputs to the deep-learning neural network, which is trained to transform them into a motion-corrected image (e.g., motion-free image).

Figure 6:
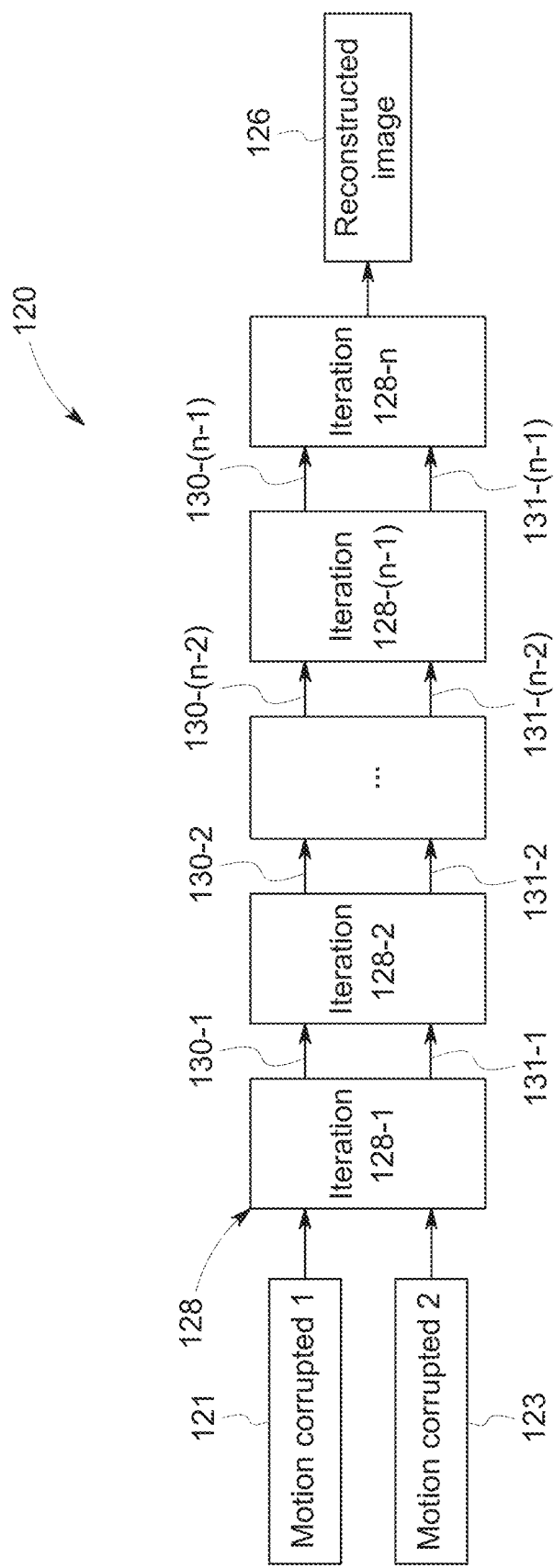
FIG. 6 is a diagrammatical representation of an embodiment of a deep-learning neural network trained to transform motion-corrupted images into motion-corrected images.
Figure 7:
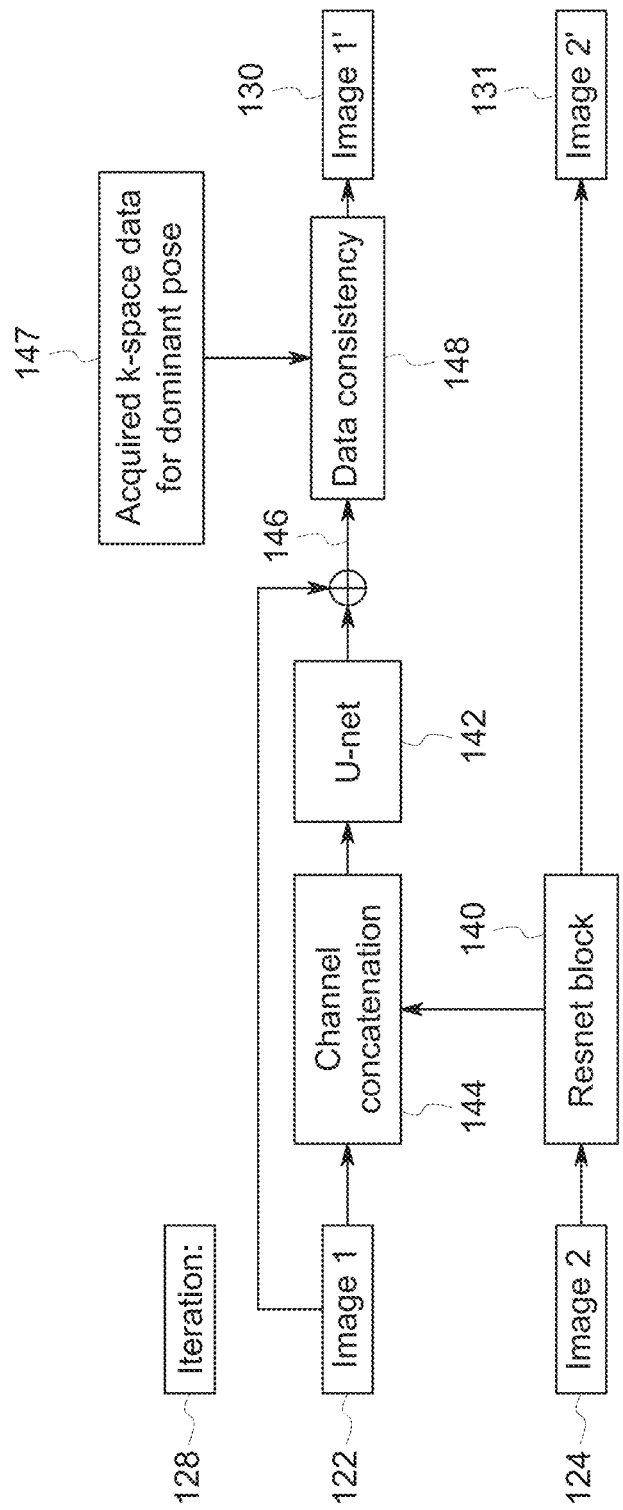
FIG. 7 is a diagrammatical representation of an embodiment of an iteration block of the deep-learning neural network of FIG. 6.

FIGS. 6 and 7 are diagrammatical representations of an embodiment of a deep-learning neural network 120 trained to transform a first sub-image 121 corresponding to a first pose (e.g., the dominant pose) and a second sub-image 123 corresponding to at least a second pose (that is, pairs of motion-corrupted sub-images corresponding to different poses), shown as "motion corrupted 1" and "motion corrupted 2," respectively, into a motion-corrected image 126, shown as "Reconstructed Image." The pose corresponding to acquisition of the dominant signal energy (from the central region of k-space) is chosen to be the first motion state or pose used for "motion corrupted 1", and k-space data from all other motion states or poses are aggregated to form "motion corrupted 2". In the embodiment illustrated in FIG. 6, the deep-learning neural network 120 includes a plurality of iteration blocks 128 to receive the first sub-image 121 (e.g., a first sub-image corresponding to a first pose) and the second sub-image 123 (e.g., a second sub-image corresponding to at least a second pose) as inputs, and to output the motion-corrected image 126.

More specifically, each iteration block 128-1-128-n (where n represents the total number of iteration blocks) of the plurality of iteration blocks 128 is arranged to receive a respective first image and a respective second image as inputs respectively, and is trained to output a respective reconstructed image from the inputs. The inputs to the entire network 120 therefore include first and second sub-images 121 and 123 (first iteration block 128-1 receives these inputs), and subsequent iteration blocks receive inputs 130-1-130-n and accompanying images 131-1-131-n. More specifically, in accordance with certain disclosed embodiments, the corresponding reconstructed image 130 produced by a particular one of the iteration blocks 128 is input to a subsequent iteration block 128 as the first image 122 (FIG. 7) for the subsequent iteration block 128. Thus, by way of reference to FIG. 6, first sub-image 121 is fed into the network 120 as a first image 122-1. Also, as an example, a reconstructed image output 130-1 of a first iteration block 128-1 is used as a first input for a second iteration block 128-2 immediately downstream of the first. In similar fashion, image 131 produced by a particular one of the iteration blocks 128 is input to a subsequent iteration block 128 as a second image 124 (FIG. 7) for the subsequent iteration block 128. Thus, by way of reference to FIGS. 6 and 7, the second sub-image 123 is fed into the network 120 as the second image 124 (FIG. 7). Also, as an example, an image output 131-1 of a first iteration block 128-1 is used as a second image 124-2 (not shown) input for a second iteration block 128-2 immediately downstream of the first. This type of arrangement continues until the motion-corrected image 126 is produced by a final iteration block 128-n as reconstructed image 130-n. Because of the input/output nature of the iteration block arrangement, the iteration blocks 128 may be considered to have a "cascaded" arrangement.

Figure 8:
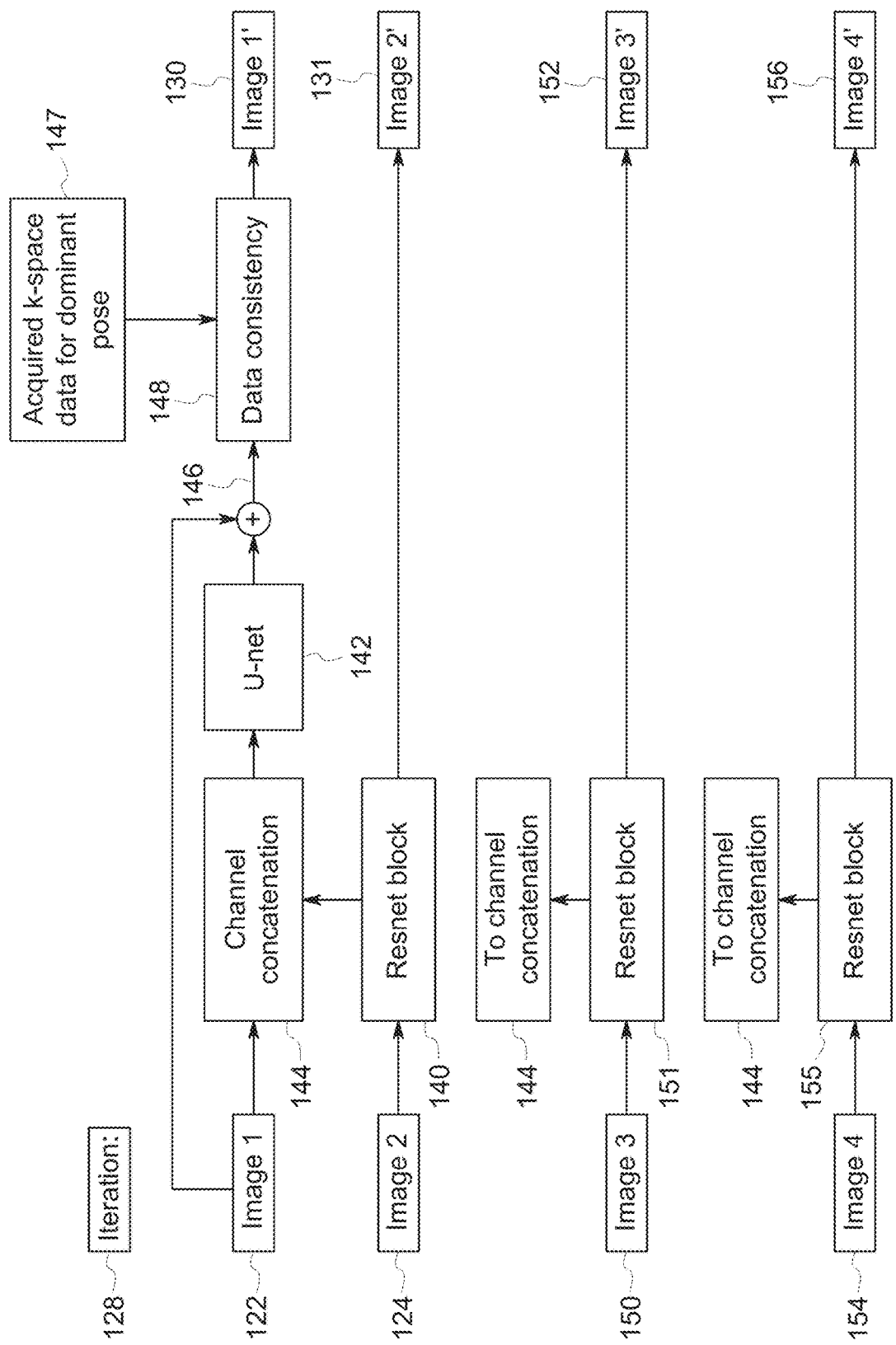
FIG. 8 is a diagrammatical representation of another embodiment of an iteration block of the deep-learning neural network of FIG. 6.

The configuration of each iteration block 128 may be further appreciated with reference to FIG. 7, which depicts the constituent components of each of the blocks 128. As shown in the illustrated embodiment, each iteration block 128 includes two neural network blocks—a residual network "Resnet" block 140 and a U-net block 142 (or U-net-like block), which are coupled by a channel concatenation block 144. In particular, the Resnet block 140 is arranged in the iteration block 128 to receive the second image 124 and to compute features from the second image 124 (which in the case of first iteration block 128-1 is the second sub-image 123 of FIG. 6) to generate the original second image together with the computed features as channels that are output to the channel concatenation block 144. Other embodiments may generate a sub-image for each non-dominant pose, rather than aggregating their k-space portions to create a single sub-image 123. In this case the iteration blocks 128 will have multiple input images. For example, FIG. 8 shows a case where k-space has been segregated into four poses. In addition to the dominant Image 1, non-dominant Images 2-4 (designated as 124, 150, 154) feed into respective Resnet blocks 140, 151, 155, whose outputs are concatenated with Image 1 in Channel Concatenation 144. Each Resnet block also outputs respective Images 2',3',4' (131, 152, 156) which are then fed to the next iteration.

In particular, this output of the Resnet block 140 is concatenated in the channel dimension with the first image 122 (which may be the first sub-image 121 of FIG. 6) by the channel concatenation block 144. Thus, the input to the U-net block 142 may be an input volume in which the channels of the second image 124, and possibly other channels, are concatenated onto the channels of the first image 122.

The U-net block 142 is a block having a multiscale convolutional neural network (CNN), and is arranged to receive the concatenated images output by the channel concatenation block 144. The U-net 142 may include a plurality of up-sampling convolutional layers and a plurality of down-sampling convolutional layers, that are useful in capturing high frequency and low-frequency motion artifacts from the concatenated image channels. In each iteration block 128, the first image 122 is combined with the output of the U-net 142 in a weighted sum to produce intermediate reconstructed image 146 with reduced motion artifacts.

The disclosed embodiments include a data consistency block 148 within each iteration block 128 to enforce consistency between the intermediate reconstructed image 146 and acquired k-space data 147 corresponding to the pose with the most signal energy (i.e., the dominant pose). Specifically, the reconstructed image 130, shown as Image 1' 130 in FIG. 7, is an image in which the acquired k-space data 147 corresponding to the dominant pose has been substituted in place of certain calculated k-space data output by the U-net block 146.

Figure 9:
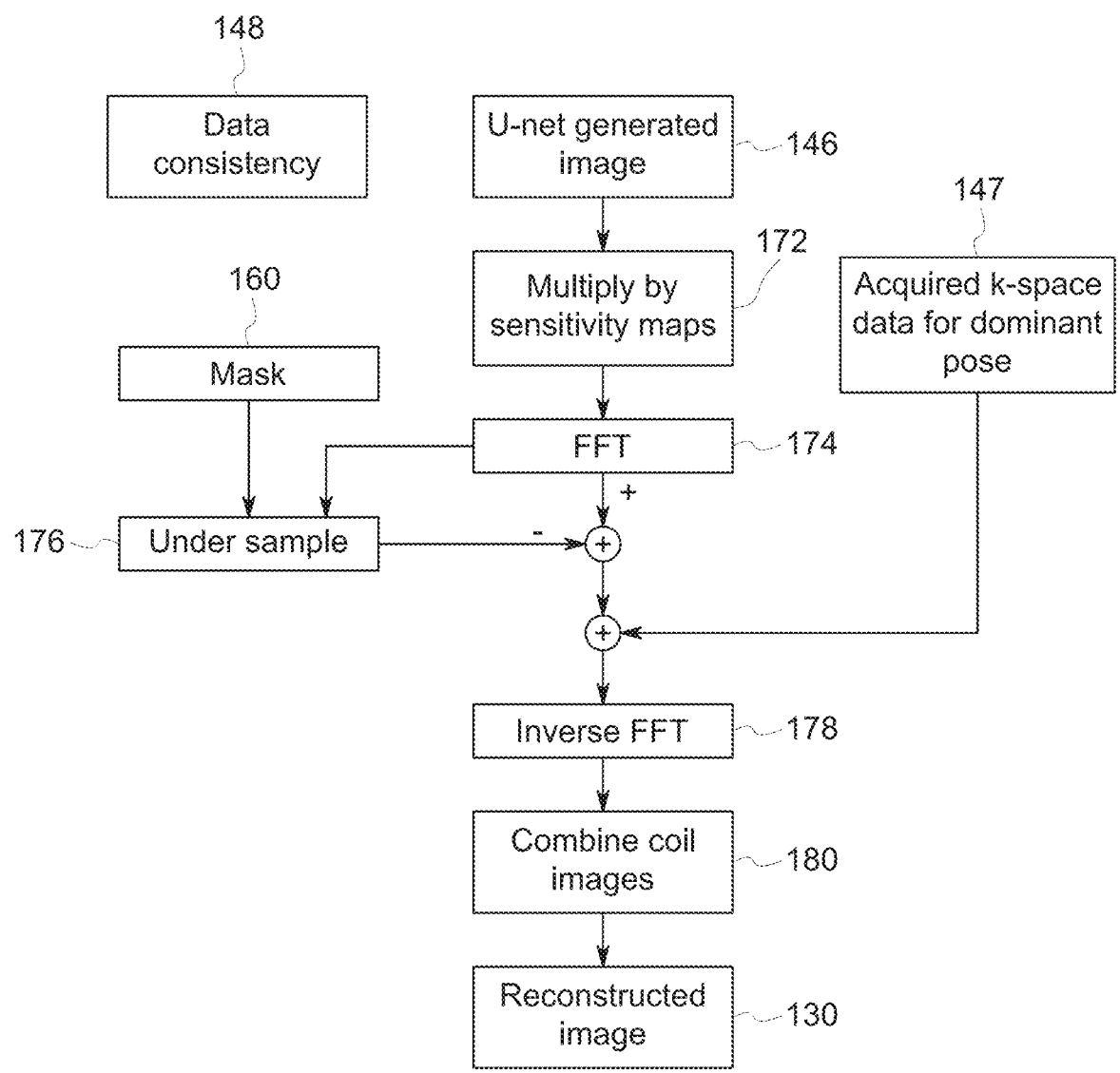
FIG. 9 is a diagrammatical representation of an embodiment of a data consistency block of the iteration block of FIGS. 7 and 8.

An embodiment of the data consistency block 148 is shown schematically in FIG. 9. In the illustrated embodiment, the U-net generated image 146 is multiplied by the sensitivity map for each receiver coil in block 172 and transformed into the spatial frequency domain (k-space) by FFT in block 174. That part of the transformed k-space data corresponding to the dominant pose is then zeroed out by subtraction. In other words, the transformed k-space data are multiplied in undersample block 176 by a binary mask 160 that denotes those k-space lines acquired for the dominant pose, and the result is then subtracted from the transformed k-space data. Next, the acquired k-space data 147 corresponding to the dominant pose are added. The net effect is to replace that part of calculated k-space corresponding to the dominant pose with the corresponding acquired k-space data. After this, the k-space data are transformed back into the image domain to generate a coil image by inverse FFT in block 178 for each receiver coil. The coil images are then combined in block 180 to generate a reconstructed image 130 as follows. Each coil image is multiplied by the complex conjugate of the corresponding sensitivity map, the multiplied coil images are summed for all receiver coils, and then the sum of the multiplied coil images is divided by the sum of squares of the sensitivity maps. Alternatively, the coil images may be combined by multiplying each coil image by the complex conjugate of the corresponding sensitivity map and then summing the multiplied coil images for all receiver coils. In an alternative embodiment, the coil images may be combined by calculating the square root of the sum of the squares of the coil images.

In an embodiment where a single coil is used for k-space data acquisition, the steps 172 and 180 may be omitted in FIG. 9. In an alternative embodiment where multiple receiver coils are used for k-space data acquisition, the steps 172 and 180 may be omitted in FIG. 9. In this case, the acquired k-space data 147 may be obtained by transforming the sub-image 121 into k-space by FFT.

In accordance with disclosed embodiments, the deep learning neural network 120 may be trained using magnetic resonance (MR) images having a known ground-truth motion-free state. Motion may be simulated by random rotations (e.g., between ±15 degrees) and shifts (e.g., between ±10 pixels). The timing of the simulated motion may be selected to fall within any time step 84 of the scan order, for example for any time step within any one of Q1-Q4. In certain embodiments, one deep-learning neural network may be constructed for each scan-order quartile. Thus, when the motion timing is known, an appropriate one of the trained neural networks corresponding to the quartile in which the first motion occurred may be selected for reconstruction. In certain embodiments, therefore, an MRI reconstruction module may include multiple deep learning neural networks that can be selected by the control and analysis circuitry of the MRI system 10 for appropriate image reconstruction.

The training of the neural networks may be conducted using a network optimization scheme, which can utilize different losses, e.g. any one of at least three loss functions (functions that measure the error between an output of the network and the ground-truth image). The first loss function is an L2-norm over the pixel distance. The second and third loss functions use the pre-trained VGG19 feature maps. The second loss function is content loss, an L2 pixelwise distance of the feature map space of the first 4-6 feature maps of the VGG19, and the third loss function is style loss, an L2 pixelwise distance of the Gram matrix constructed over the feature maps of the first 5 layers of the VGG19 network.

Example

Figure 10A:
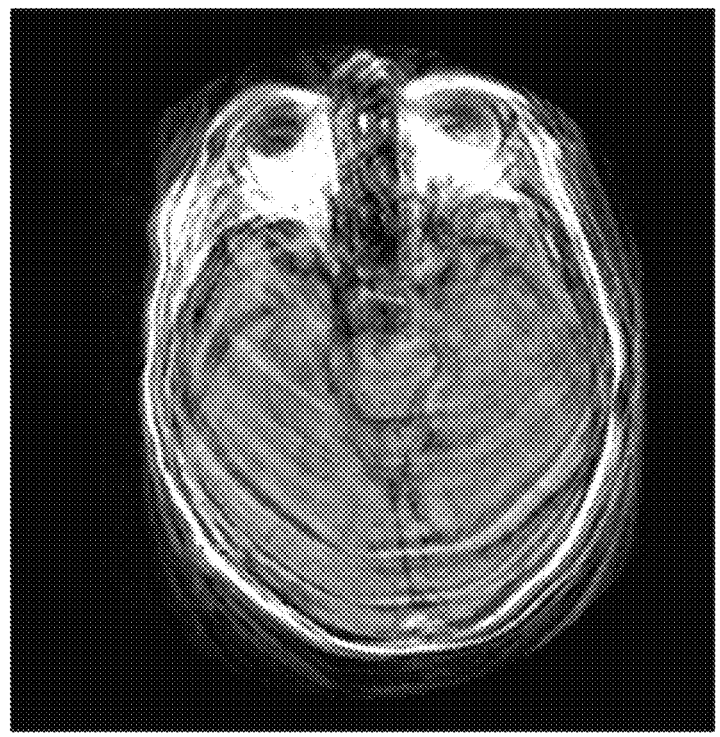
FIGS. 10A-10C provide a comparative illustration of a motion-corrupted image (a) where motion occurred in Q2 and a corresponding motion-corrected image (b) compared to the ground-truth image (c)
Figure 10B:
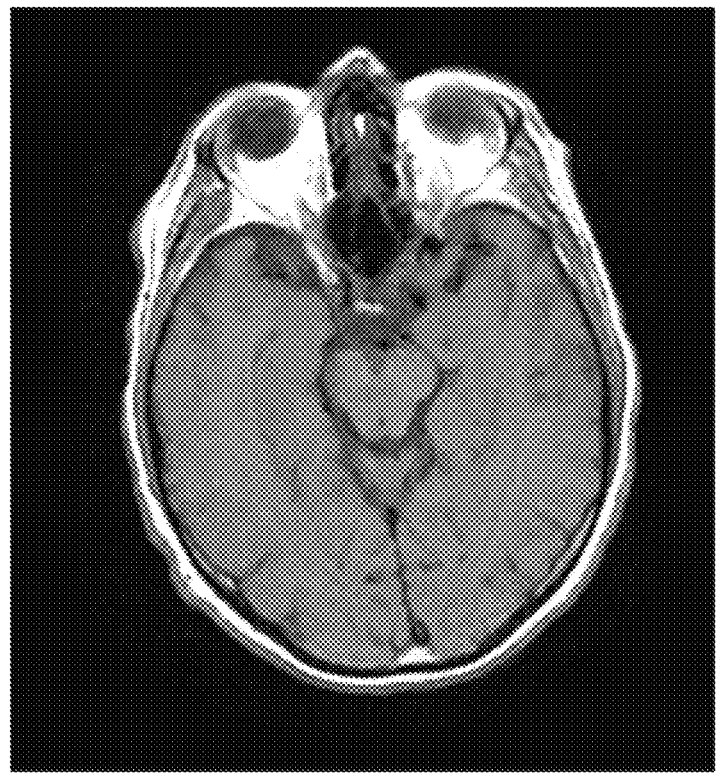
Figure 10C:

A training data set was constructed from approximately 7000 MR images. Four data sets of about 7000 images each were created by randomly selecting for each image a motion timing for any time step 84 within Q1 to Q4, a random shift (between ±10 pixels) and a random rotation (between ±15 degrees). For each quartile a separate deep learning neural network having the architecture of FIGS. 6 and 7 was trained. Performance was measured on validation and test data sets of about 500 images each. The normalized mean squared error (NMSE), style loss, and content loss were used to measure performance. The NMSE was found to be correlated with the timing of the motion, getting bigger toward the center of k-space, where the low spatial frequencies with most energy are located. FIGS. 10A-10C show an example of a motion-corrupted image (a) where motion occurred in Q2 at timestep 90 and corresponding motion-corrected image (b) compared to the ground-truth image (c).

Figure 11:
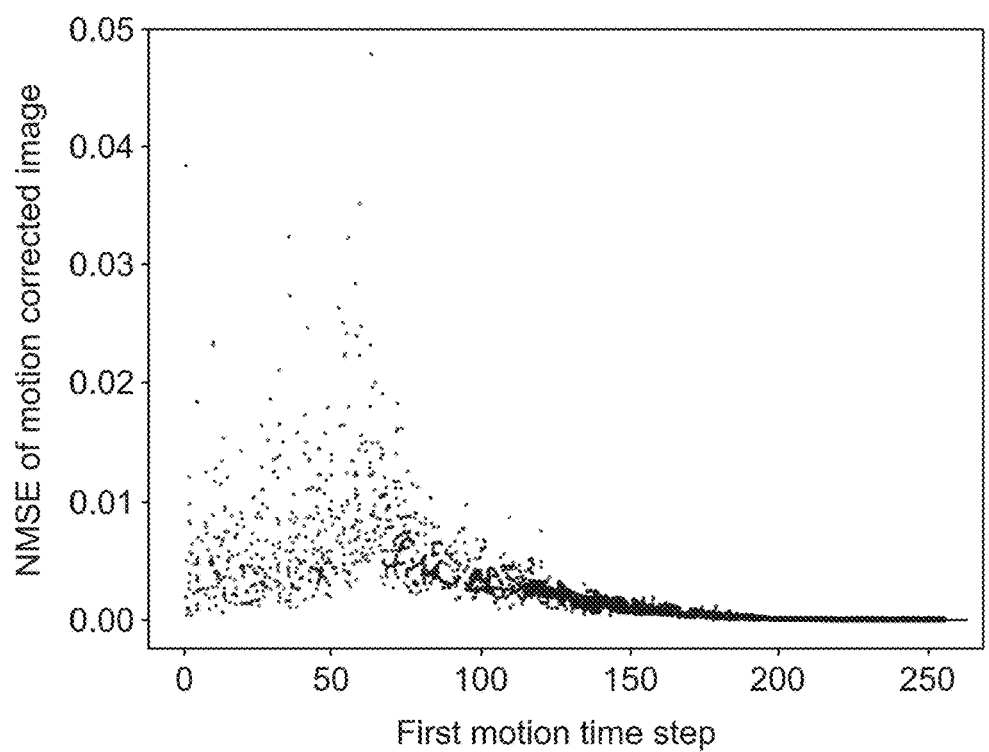
FIG. 11 is a plot of normalized mean squared error (NMSE) as a function of first motion time step depicting results of correction of simulated-motion test sets with two or three random motions during the scan using the deep-learning neural network architecture of FIGS. 6-8.

Results of correction of simulated-motion test sets with two or three random motions during the scan are shown in FIG. 11. Specifically, FIG. 11 shows the NMSE of repaired images relative to ground truth, as a function of timing of the first motion step. The average NMSE (FIGS. 10A-10C) was $8\times10^{-3}$ for Q1, $5.9\times10^{-3}$ for Q2, $1\times10^{-3}$ for Q3, and $1.4\times 10^{-4}$ for Q4. In the most difficult cases, with motion near center k-space, small residual motion artifacts sometimes remained visible in the repaired images.

Technical effects of the invention include, but are not limited to, enabling the automatic real-time correction of motion corrupted images, making them clinically useable. This creates substantial value by improving the throughput of the MRI scanners, improving the patient's experience and reducing burden on the MR technologist.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A magnetic resonance imaging (MRI) method comprising:
    dividing k-space data from a motion-corrupted Mill scan into a first portion and a second portion based on timing associated with transition between poses, and a predetermined scan order, wherein the predetermined scan order defines how k-space is filled as a function of time step for the motion-corrupted MM scan, wherein the first portion includes a central region of k-space data;
    reconstructing a first sub-image and a second sub-image from the first portion and the second portion, respectively;
    providing the first sub-image and the second sub-image as inputs to a neural network, wherein the neural network includes a plurality of iteration blocks and the first sub-image and the second sub-image are provided as inputs to a first iteration block of the neural network; and
    transforming the first sub-image and the second sub-image into a motion-corrected image using the neural network.

2. The method of claim 1, wherein reconstructing the first sub-image and the second sub-image comprises reconstructing a pre-motion zero-filled sub-image and a post-motion zero-filled sub-image.

3. The method of claim 1, wherein dividing k-space data from the motion-corrupted MRI scan into the first portion and the second portion comprises segregating k-space data from a single pose for the first portion based on signal energy.

4. The method of claim 1, wherein each iteration block of the plurality of iteration blocks ends with a data consistency block that ensures that an image output by the respective iteration blocks contains k-space data associated with a single pose that holds the most signal energy relative to other k-space data collected during the motion-corrupted scan.

5. The method of claim 4, wherein each iteration block of the plurality of iteration blocks comprises a U-net architecture, having a multiscale convolutional neural network (CNN) trained to generate an image, wherein the multiscale CNN comprises a plurality of down-sampling convolutions and a plurality of up-sampling convolutions.

6. The method of claim 4, wherein the data consistency block overwrites k-space portions of an image generated earlier in the iteration with corresponding portions taken from k-space data of the single pose that holds the most signal energy.

7. The method of claim 6, comprising providing multi-coil k-space data from which the first sub-image was calculated to the data consistency block of the neural network, and providing the second sub-image to a residual network block of a first iteration of the plurality of iterations.

8. The method of claim 7, wherein providing the first sub-image and the second sub-image as inputs to the neural network comprises providing the first sub-image to a channel concatenation block of the first iteration where the first sub-image is concatenated with an output of the residual network block.

9. The method of claim 8, wherein reconstructing the first sub-image and the second sub-image from the first portion and the second portion comprises reconstructing the second sub-image and additional sub-images from the second portion by dividing the second portion into individual sets of k-space data each corresponding to a single pose and reconstructing the individual sets of k-space data, and wherein providing the first sub-image and the second sub-image as inputs to the neural network comprises providing the second sub-image and the additional sub-images to respective residual network blocks.

10. The method of claim 1, wherein each of the iteration blocks includes two input terminals and two output terminals.

11. The method of claim 1, wherein the first sub-image and the second sub-image are provided as inputs to a first input terminal and a second input terminal of the first iteration block of the neural network respectively.

12. A magnetic resonance imaging (MRI) method comprising:
producing a first sub-image and a second sub-image from a motion-corrupted set of k-space data representing a plurality of poses for an imaged subject via a process comprising:
identifying a portion of the motion-corrupted set of k-space data corresponding to a dominant pose;
generating the first sub-image from the identified portion of the motion-corrupted set of k-space data;
grouping remaining portions of the motion-corrupted set of k-space data corresponding to other poses together; and
generating the second sub-image from the remaining grouped portions of the motion-corrupted set of k-space data;
inputting the first sub-image and the second sub-image to a neural network trained to transform pairs of motion-corrupted sub-images into motion-corrected images, wherein the neural network includes a plurality of iteration blocks and the first sub-image and the second sub-image are provided as inputs to a first iteration block of the neural network;
transforming the first sub-image and the second sub-image into a motion-corrected image using the neural network; and
wherein the portion of the motion-corrupted set of k-space data corresponding to a dominant pose includes a central region of the motion-corrupted set of k-space data.

13. The method of claim 12, comprising imposing a constraint that regions of k-space corresponding to the dominant pose are not changed by the neural network, using a data consistency block of the neural network.

14. The method of claim 12, wherein generating the first sub-image from the identified portion of the motion-corrupted set of k-space data comprises zero-filling those regions of k-space not corresponding to the dominant pose, and transforming resulting zero-filled k-space data corresponding to the dominant pose into the image domain.

15. The method of claim 12, wherein inputting the first sub-image and the second sub-image to the neural network comprises inputting the second sub-image to a residual network block of the neural network and inputting the first sub-image to a channel concatenation block of the neural network that concatenates the first sub-image with an output from the residual network block.

16. A magnetic resonance imaging (MRI) reconstruction module comprising:
circuitry programmed to implement a trained neural network for transformation of motion-corrupted images into motion-corrected images;
a plurality of iteration blocks of the trained neural network, wherein the trained neural network receives a first sub-image corresponding to a first pose and a second sub-image corresponding to at least a second pose as inputs, and wherein the trained neural network outputs a motion-corrected image;
a data consistency block of each iteration block of the plurality of iteration blocks, wherein the data consistency block is programmed to produce a reconstructed image where line locations in k-space that correspond to the first pose are overwritten with k-space data from the first pose;
wherein the first pose includes a pre-motion state, and the second pose includes a post-motion state; and
wherein the trained neural network includes a plurality of iteration blocks and the first sub-image and the second sub-image are provided as inputs to a first iteration block of the trained neural network.

17. The MRI reconstruction module of claim 16, wherein each iteration block of the plurality of iteration blocks receives a respective first image and a respective second image, and outputs a respective reconstructed image having fewer motion-related artifacts compared to an image generated from k-space data produced by combining k-space data of the respective first image and the respective second image, and wherein the plurality of iteration blocks is arranged such that the respective reconstructed image produced by each iteration block is used as the respective first image for a subsequent iteration block of the plurality of iteration blocks until the motion-corrected image is output by a final iteration block of the plurality of iteration blocks.

18. The MRI reconstruction module of claim 17, comprising a U-net of each iteration block of the plurality of iteration blocks located upstream of the data consistency block of the respective iteration block, the U-net having a multiscale convolutional neural network (CNN) trained to generate an image with reduced artifacts, wherein the multiscale CNN comprises a plurality of down-sampling convolutions and a plurality of up-sampling convolutions and wherein the data consistency block is programmed to produce the reconstructed image from the image with reduced artifacts.

19. The MRI reconstruction module of claim 18, comprising:
a residual network block for each iteration block to output the second image together with additional features computed from the respective second image to a channel concatenation block of the respective iteration block; and
the channel concatenation block of each iteration block, to concatenate in the channel dimension the respective first image and the output from the residual network, and to provide the concatenated output to the U-net.

20. The MRI reconstruction module of claim 19, wherein the data consistency block of each iteration block of the plurality of iteration blocks is programmed to receive the image with reduced artifacts from the respective U-net of the respective iteration block, the acquired k-space data corresponding to the first sub-image input to the plurality of iteration blocks, and a mask that contains information on which lines in k-space correspond to the first sub-image or the second sub-image.

21. The Mill reconstruction module of claim 16, wherein the circuitry is programmed to generate the first sub-image and the second sub-image by a process comprising:
dividing k-space data obtained from an MRI scan into first k-space data and second k-space data based on timing associated with motion occurring during the MRI scan and a scan order, the first k-space data corresponding to a single motion state and the second k-space data corresponding to all remaining motion states, and wherein the scan order defines k-space filling as a function of time step;
reconstructing the first k-space data into the first sub-image; and
reconstructing the second k-space data into the second sub-image.

* * * * *